(12) United States Patent
Dellock et al.

(10) Patent No.: US 10,773,690 B2
(45) Date of Patent: Sep. 15, 2020

(54) CLEANING A VEHICLE DISPLAY

(71) Applicant: Ford Global Technologies, LLC, Dearborn, MI (US)

(72) Inventors: Paul Kenneth Dellock, Northville, MI (US); Stuart C. Salter, White Lake, MI (US); David Brian Glickman, Southfield, MI (US); Annette Lynn Huebner, White Lake, MI (US); Venkatesh Krishnan, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 208 days.

(21) Appl. No.: 15/636,024

(22) Filed: Jun. 28, 2017

(65) Prior Publication Data
US 2019/0001930 A1      Jan. 3, 2019

(51) Int. Cl.
| | | |
|---|---|---|
| *B60S 1/56* | (2006.01) | |
| *A61L 2/08* | (2006.01) | |
| *A61L 2/10* | (2006.01) | |
| *A61L 2/24* | (2006.01) | |
| *G02B 27/00* | (2006.01) | |
| *B60S 1/64* | (2006.01) | |

(52) U.S. Cl.
CPC ............... *B60S 1/56* (2013.01); *A61L 2/088* (2013.01); *A61L 2/10* (2013.01); *A61L 2/24* (2013.01); *G02B 27/0006* (2013.01); *A61L 2202/11* (2013.01); *A61L 2202/14* (2013.01); *A61L 2202/16* (2013.01); *A61L 2202/17* (2013.01); *A61L 2202/20* (2013.01); *B60S 1/64* (2013.01)

(58) Field of Classification Search
None
See application file for complete search history.

(56) References Cited

U.S. PATENT DOCUMENTS

| | | |
|---|---|---|
| 6,690,268 B2 | 2/2004 | Schofield et al. |
| 8,147,971 B2 | 4/2012 | Van Herpen |
| 8,951,614 B2 | 2/2015 | Collins et al. |
| 9,785,192 B1 * | 10/2017 | Cheng .................. G06F 1/1643 |
| 2003/0073042 A1 | 4/2003 | Cernigliaro et al. |
| 2004/0160762 A1 | 8/2004 | Fuwausa |
| 2006/0087826 A1 | 4/2006 | Anderson |
| 2006/0158735 A1 | 7/2006 | Tonar et al. |

(Continued)

FOREIGN PATENT DOCUMENTS

| | | | |
|---|---|---|---|
| CN | 102555328 A | * | 7/2012 |
| CN | 202905045 U | | 4/2013 |

(Continued)

OTHER PUBLICATIONS

Non-Final Office Action dated Nov. 1, 2018 for U.S. Appl. No. 15/636,006 (32 pages).
Search Report from United Kingdom Intellectual Property Office dated Dec. 14, 2018 regarding Application No. GB1810513.0 (7 pages).
Search Report from United Kingdom Intellectual Property Office dated Dec. 24, 2018 regarding Application No. GB1810511.4 (9 pages).
Notice of Allowance dated Apr. 11, 2019 regarding U.S. Appl. No. 15/636,006 (28 pages).

*Primary Examiner* — David P. Merlino
(74) *Attorney, Agent, or Firm* — Frank A. MacKenzie; Bejin Bieneman PLC

(57) ABSTRACT

A computer having a processor and memory storing instructions executable by the processor that include: to determine whether a vehicle cabin is occupied; and based on the determination, to control actuation of a lamp, located on a bezel of a display, to impinge upon a screen having a light-sensitive coating.

19 Claims, 9 Drawing Sheets

(56) References Cited

U.S. PATENT DOCUMENTS

| | | | | |
|---|---|---|---|---|
| 2008/0158510 | A1* | 7/2008 | Tant | B60K 35/00 353/14 |
| 2010/0148695 | A1* | 6/2010 | Hsieh | B01J 19/123 315/294 |
| 2011/0256019 | A1* | 10/2011 | Gruen | A61L 2/10 422/24 |
| 2013/0045132 | A1* | 2/2013 | Tumanov | A61L 2/10 422/24 |
| 2014/0286048 | A1* | 9/2014 | Riello | G09F 13/18 362/608 |
| 2015/0182647 | A1* | 7/2015 | Ranta | A61L 2/10 250/338.1 |
| 2015/0258228 | A1* | 9/2015 | Cohen | A61L 2/10 345/178 |
| 2015/0286085 | A1* | 10/2015 | Davis | G02F 1/13718 349/12 |
| 2016/0221440 | A1* | 8/2016 | Tane | G01D 11/28 |
| 2016/0357281 | A1* | 12/2016 | Fleizach | H04N 3/155 |
| 2017/0224853 | A1* | 8/2017 | Jay | A61L 2/10 |
| 2018/0031740 | A1 | 2/2018 | Alarcon et al. | |
| 2018/0348509 | A1* | 12/2018 | Carpenter | G02B 27/0006 |

FOREIGN PATENT DOCUMENTS

| | | |
|---|---|---|
| EP | 0368450 A2 | 5/1990 |
| JP | 2000010491 A | 1/2000 |
| JP | 2000352947 A | 12/2000 |
| JP | 2001096167 A | 4/2001 |
| JP | 2004219969 A | 8/2004 |
| JP | 2007315954 A | 12/2007 |
| JP | 2007331546 A | 12/2007 |
| JP | 2012254673 A | 12/2012 |
| KR | 100740903 B1 | 7/2007 |
| WO | WO 03033037 A1 | 4/2003 |
| WO | 2017204774 A1 | 11/2017 |

* cited by examiner

CLEANING A VEHICLE DISPLAY

BACKGROUND

During normal use, dust, fingerprints, and other fluids can adhere to the surfaces of a vehicle display. To clean such contaminants, the user of the vehicle conventionally manually applies a soft cloth which may or may not have a cleaning solution thereon.

DETAILED DESCRIPTION

Figure 1:
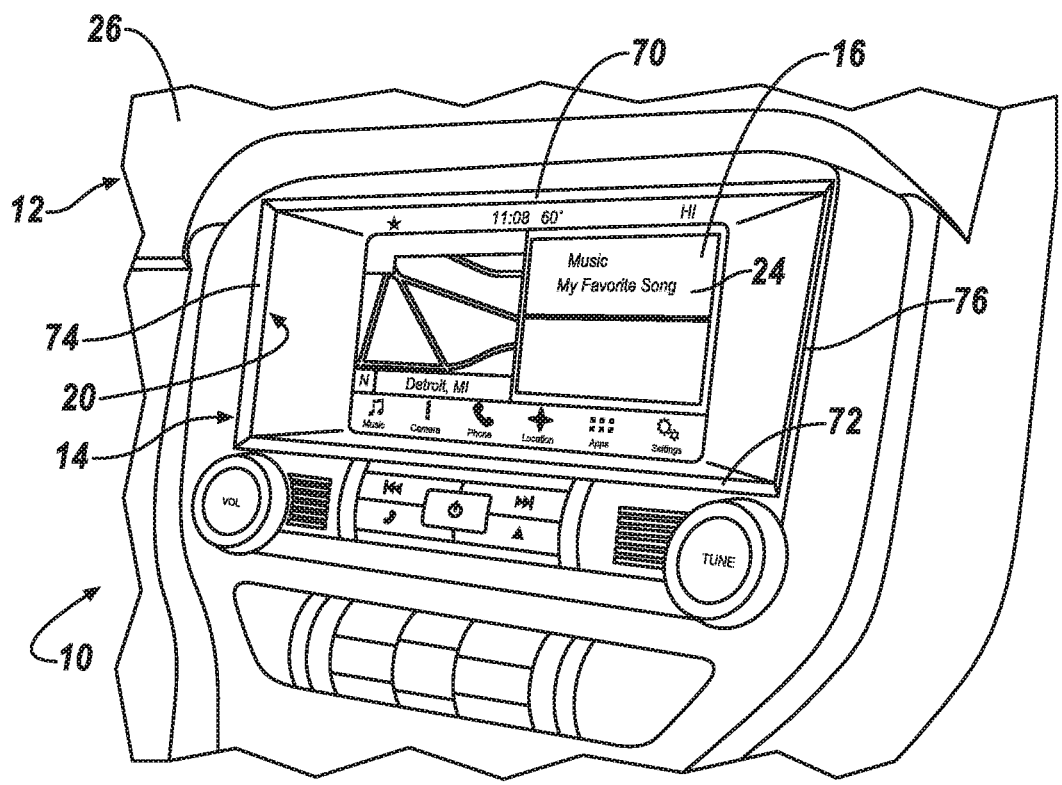
FIG. 1 illustrates an interior cleaning system that includes a display carried by an instrument panel of a vehicle.

An interior cleaning system for a vehicle is described that includes a computer and a display, coupled to the computer—the display having a bezel that includes a lamp which directs light toward a screen of the display to clean a surface thereof. According to one illustrative example, the computer includes a processor and memory storing executable instructions that include: to determine that a vehicle cabin is occupied; to determine that an ambient light in the cabin is greater than a first threshold; and based on the determinations, to actuate a lamp in a display having a light-sensitive coating on a screen thereof so that light from the lamp activates the coating.

According to the at least one example set forth above, the instructions further include: to use a timer to measure a predetermined interval of time, wherein lamp actuation is based in part on an expiration of the interval.

According to the at least one example set forth above, the instructions further include: to execute a counter to quantify a number of user-touches of the screen, wherein lamp actuation is based in part on the number exceeding a second threshold.

According to the at least one example set forth above, the instructions further include: to count the number of user-touches in a plurality of user-touch regions; to determine that the number of user-touches in one of the plurality of user-touch regions exceeds the threshold; and to control the actuation of at least one light source of the lamp so that light therefrom impinges upon the respective region.

According to the at least one example set forth above, the instructions further include: to determine that a first user-touch and a second user-touch occur within a predetermined touch-interval; and in response thereto, to count the second user-touch as less than one incrementation of the counter.

According to the at least one example set forth above, the instructions further include: to determine that a contact region of the screen maintains a surface charge that is greater than a second threshold for at least a predetermined period of time; and in response thereto, to actuate the lamp.

According to the at least one example set forth above, a system includes: the computer and the display, wherein light from the lamp is directed axially and radially-inwardly from the bezel and toward a cover of the screen that includes the coating.

According to the at least one example set forth above, the coating comprises titanium dioxide ($TiO_2$), wherein the lamp emits light at a wavelength within 310-390 nanometers (nm).

According to another illustrative example, a computer includes a processor and memory storing executable instructions that include: to determine whether a vehicle cabin is occupied; and based on the determination, to control actuation of a lamp, located on a bezel of a display, to impinge upon a screen having a light-sensitive coating.

According to the at least one example set forth above, a system includes: the computer and the display, wherein light from the lamp is directed axially and radially-inwardly from the bezel and toward a cover of the screen that includes the coating.

According to the at least one example set forth above, the coating comprises titanium dioxide ($TiO_2$), wherein the lamp emits light at a wavelength within 310-390 nanometers (nm).

According to the at least one example set forth above, the instructions further include: to determine that the cabin is occupied; to determine that an ambient light within the cabin exceeds a threshold; and based on the determinations, to control the actuation.

According to the at least one example set forth above, controlling the actuation further is based on an instruction to determine that a state of a transmission is in PARK.

According to the at least one example set forth above, the instructions further include: to use a timer to measure a predetermined interval of time, wherein controlling the actuation is based in part on an expiration of the interval.

According to the at least one example set forth above, the instructions further include: to execute a counter to quantify a number of user-touches of the screen, wherein controlling the actuation is based in part on the number exceeding a predetermined threshold.

According to the at least one example set forth above, the instructions further include: to count the number of user-touches in a plurality of user-touch regions; to determine that the number of user-touches in one of the plurality of user-touch regions exceeds the threshold; and to control the actuation of at least one light source of the lamp so that light therefrom impinges upon the respective region.

According to the at least one example set forth above, the instructions further include: to determine that a first user-touch and a second user-touch occur within a predetermined touch-interval; and in response thereto, to count the second user-touch as less than one incrementation of the counter.

According to the at least one example set forth above, the instructions further include: to determine that a contact region of the screen maintains a surface charge that is greater than a threshold for at least a predetermined period of time; and in response thereto, to control the actuation.

According to the at least one example set forth above, the threshold includes a baseline value of nominal surface charge for a plurality of contact regions of the screen.

According to the at least one example set forth above, the instructions further include: to receive an indication of a manual actuation from a switch coupled to the display; and in response thereto, to control the actuation.

According to the at least one example, a computer is disclosed that is programmed to execute any combination of the examples set forth above.

According to the at least one example, a method is disclosed that includes any combination of the instructions set forth above.

According to the at least one example, a computer program product is disclosed that includes a computer readable medium storing instructions executable by a computer processor, wherein the instructions include any combination of the instruction examples set forth above.

Figure 2:
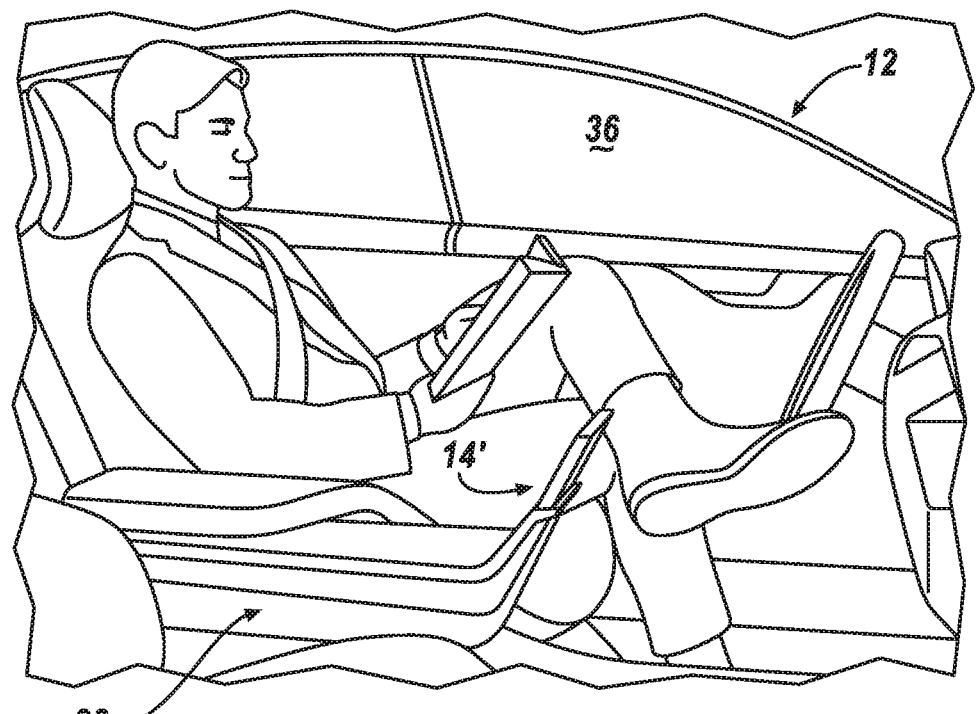
FIG. 2 illustrates an occupant in a cabin of the vehicle and a similar display carried by a center console.

Now turning to the figures, wherein like numerals indicate like parts throughout the several views, there is shown an interior cleaning system 10 for a vehicle 12 that comprises a display 14 that includes a screen 16 having a light-sensitive coating 18 and a bezel 20 having a lamp 22 which emits light at a frequency that activates the coating 18 to clean or sanitize a surface 24 of the screen. The display 14 may be carried by a vehicle instrument panel 26 (e.g., as shown in FIG. 1) or may be located elsewhere (e.g., such as display 14' coupled to a center console 28, as shown in FIG. 2). In at least some examples, the screen 16 is a touchscreen which may be used by a number of different users (e.g., consider examples where vehicle 12 is an autonomous taxi or rideshare vehicle). As described more below, when actuated, the lamp 22 of the display 14 may project light which kills or neutralizes living organic matter on the surface 24 of screen 16 (e.g., kills bacteria and viruses on the screen from sweat, saliva, etc. of the different users). According to one non-limiting example, the light-sensitive coating 18 may comprise titanium dioxide and the frequency emitted by lamp 22 may be in the ultraviolet (UV) band. Hence, the UV light may kill the living organic matter, while the titanium dioxide (in the presence of UV light) may react with carbon-based matter located on the surface 24 of screen 16 (e.g., such as bacteria, viruses, saliva, sweat, and other human bodily fluids) yielding a water vapor and carbon dioxide gas by-product. As described below, other light-sensitive coatings and/or other light wavelengths could be used instead.

Vehicle 12 is shown as a passenger car; however, vehicle 12 could also be a truck, sports utility vehicle (SUV), recreational vehicle, bus, train, marine vessel, aircraft, or the like that includes the interior cleaning system 10. Vehicle 12 may be operated in any one of a number of autonomous modes. In at least one example, vehicle 12 may operate as an autonomous taxi, a ride-sharing vehicle, an autonomous school bus, or the like—e.g., operating in a fully autonomous mode (e.g., a level 5), as defined by the Society of Automotive Engineers (SAE) (which has defined operation at levels 0-5). For example, at levels 0-2, a human driver monitors or controls the majority of the driving tasks, often with no help from the vehicle 12. For example, at level 0 ("no automation"), a human driver is responsible for all vehicle operations. At level 1 ("driver assistance"), the vehicle 12 sometimes assists with steering, acceleration, or braking, but the driver is still responsible for the vast majority of the vehicle control. At level 2 ("partial automation"), the vehicle 12 can control steering, acceleration, and braking under certain circumstances without human interaction. At levels 3-5, the vehicle 12 assumes more driving-related tasks. At level 3 ("conditional automation"), the vehicle 12 can handle steering, acceleration, and braking under certain circumstances, as well as monitoring of the driving environment. Level 3 may require the driver to intervene occasionally, however. At level 4 ("high automation"), the vehicle 12 can handle the same tasks as at level 3 but without relying on the driver to intervene in certain driving modes. At level 5 ("full automation"), the vehicle 12 can handle all tasks without any driver intervention.

Interior cleaning system 10 may include an occupancy detection system 30, a vehicle powertrain system 32, the display 14 (described in detail below), and a computer 40 which may form part of the display 14 (e.g., within a common module) or which may be coupled electrically thereto. Occupancy detection system 30 and powertrain system 32 may provide relevant data to computer 40 so that computer 40 may manage the cleaning of display 14; in addition, systems 30-32 may facilitate vehicle 12 operating in a fully autonomous mode.

Occupancy detection system 30 may comprise at least one computer 34 electrically coupled to a number of sensors (e.g., not shown). Computer 34 may receive data from seat-belt sensors, seat pressure sensors, cabin cameras or imaging sensors (e.g., aimed at vehicle seating to detect occupancy), proximity sensors, and the like. In general, computer 34 may analyze the data from one or more sensors to determine whether a cabin 36 of vehicle 12 is empty or occupied, e.g., using techniques known to those skilled in the art. Further, computer 34 may provide an output (e.g., an analog or digital signal) to interior cleaning system 10 that indicates the cabin state (e.g., 'empty' or 'occupied'). Computer 34 further may indicate whether an occupant is currently ingressing or egressing the cabin using door sensors, vision sensors, proximity sensors, or the like.

Powertrain system 32 may comprise at least one computer 38 electrically coupled to a vehicle engine (not shown) and a vehicle transmission (not shown). According to at least one example, computer 38 may provide, to the interior cleaning system 10, an output (e.g., an analog or digital signal) indicating a state of the engine. For example, when the engine is running, the state may be ON, and when the engine is not running, the state may be OFF. As explained more below, in at least one example, computer 40 may clean display 14 when the vehicle engine state is ON. The term vehicle engine should be construed broadly to include a combustion engine, a hybrid electric engine, an electric engine or motor(s), a solar-electric engine, or the like.

Interior cleaning system 10 of vehicle 12 may include other systems (not shown) as well which facilitate operation of the vehicle in a fully autonomous mode. Non-limiting examples of systems related to autonomous driving include one or more vision and/or imaging systems, additional sensing systems (e.g., in addition to occupancy detection system 30), one or more wireless vehicle communication systems, a vehicle steering system, a vehicle braking system, one or more vehicle safety systems, and the like. In some examples, these systems related to autonomous driving may be controlled collectively by a master computing device; in other examples, no master computing device exists (e.g., instead the systems interact directly or via a mesh communication network). Thus, for example, each system related to autonomous driving may comprise one or more system computing devices which interact with one another to control autonomous or driver-less vehicle operation. Consequently, according to one example, the vehicle 12 may be controlled collectively by the systems to drive in a fully autonomous mode to pick up a vehicle user (e.g., according to a request sent from the user to the vehicle 12). Once the user is in vehicle 12, the systems related to autonomous driving may cause the vehicle 12 deliver the user to a predetermined location (e.g., according to his/her request). While in the vehicle, neither the user or other occupants may need to exhibit control over any combination of the systems described above. According to one example, as described more below, the user may enter destination data into the display 14 and/or while traveling from origination location to destination location, the user may use the display to receive information services, entertainment services, the like, or any combination thereof. The term user, as used herein, means a licensee or other authorized person within vehicle 12; further, the term user (within vehicle 12) and occupant may be used interchangeably.

Computer 40 may comprise at least one processor 42 and memory 44 coupled to the processor 42, wherein memory 44 stores instructions executable by the processor 42. For example, processor 42 can be any type of device capable of processing electronic instructions, non-limiting examples including a microprocessor, a microcontroller or controller, an application specific integrated circuit (ASIC), etc.—just to name a few. In general, computer 40 may be programmed to execute digitally-stored instructions, which may be stored in memory 44, which enable the computer 40, among other things, to receive an indication that the vehicle engine state is ON (e.g., from powertrain system 32) and to receive an indication that the vehicle is in an unoccupied state (e.g., from occupancy detection system 30), and based on these indications, to actuate the lamp 22 (e.g., causing light from the lamp to be directed toward the surface 24 of the screen 16, thereby sanitizing the surface 24). Computer 40 may be programmed to carry out other instructions as well—e.g., including selectively controlling one or more light sources (discussed below) of lamp 22, controlling the wavelengths of light emitted from the lamp 22, actuating the lamp 22 based on a cleaning schedule, actuating the lamp 22 based on a quantity of user-touches, actuating the lamp 22 based on a capacitance of a finger contact region of screen 16, and actuating the lamp 22 based on a manual switch actuation (e.g., by an authorized vehicle service technician), just to name a few non-limiting examples.

Memory 44 may include any non-transitory computer usable or readable medium, which may include one or more storage devices or articles. Exemplary non-transitory computer usable storage devices include conventional computer system RAM (random access memory), ROM (read only memory), EPROM (erasable, programmable ROM), EEPROM (electrically erasable, programmable ROM), as well as any other volatile or non-volatile media. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read. As discussed above, memory 44 may store one or more computer program products which may be embodied as software, firmware, or the like.

Figure 3:
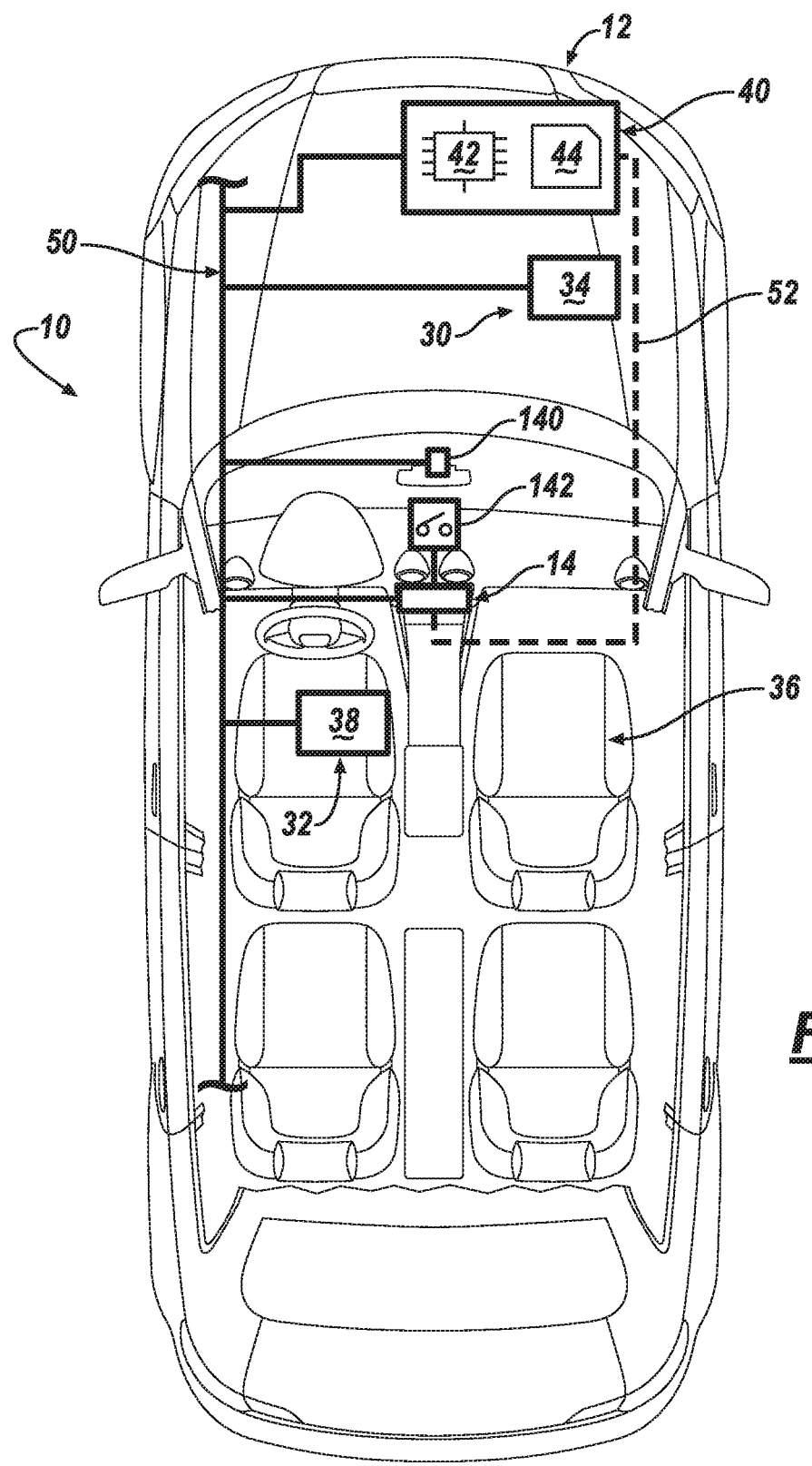
FIG. 3 is a schematic diagram of the vehicle illustrating a network connection coupling the display of FIG. 1 to one or more vehicle system computers.

FIG. 3 illustrates a wired and/or wireless vehicle network connection 50 which enables, among other things, communication between computer 34 (of occupancy detection system 30), computer 38 (of powertrain system 32), and computer 40 and/or display 14. In at least one example, the connection 50 includes one or more of a controller area network (CAN) bus, Ethernet, Local Interconnect Network (LIN), a fiber optic connection, a Bluetooth or Bluetooth Low Energy (BLE) connection, a Wi-Fi or Wi-Fi Direct connection, or the like. Other examples also exist. Aspects of connection 50 may be standardized; other aspects may be proprietary; and of course, combinations thereof are possible as well. Network connection 50 may facilitate intra-vehicular system communication—e.g., enabling display computer 40 to receive data regarding, e.g., engine state (e.g., from computer 38) and/or vehicle occupancy state (e.g., from computer 34). FIG. 3 further illustrates that connection 50 may comprise discrete wired or wireless connections as well. For example, computer 40 may be communicatively coupled to display 14 by bus 50, by discrete connection 52, or a combination thereof.

Turning now to display 14 (FIGS. 4, 4A, 4B), the display may comprise a multi-layer screen 16 overlaid by (or abutting) bezel 20—e.g., at a periphery 54 thereof. The screen 16 may be a touchscreen; however, this is not required. For example, screen 16 may be a capacitive touchscreen, a resistive touchscreen, or the like. For purposes of illustration only, and not intending to be limiting, an example of a capacitive touchscreen is described below.

Screen 16 may comprise the light-sensitive coating 18 and an electronics portion 56 that includes: a lens or cover 58, a film 60 (e.g., a capacitive or resistive film), a liquid crystal display (LCD) 62, and a backlight 64. The cover 58 may be a transparent sheet of plastic, resin, glass, etc. which protects the film 60, LCD 62, and backlight 64 therebeneath. The capacitive film 60 may comprise an electrical circuit that includes a plurality of capacitive elements (not shown) responsive to the electrical energy carried by a human fingertip when the user's fingertip touches the cover 58. LCD 62 can include an electrically-modulated optical device using liquid crystal to provide an image outwardly (i.e., into the cabin 36) through the cover 58 when light is projected from the backlight 64 (e.g., which may comprise an optical waveguide, a light source, a driver circuit for the light source, etc.—none of which are shown). According to one arrangement, the film 60 and LCD 62 are sandwiched between the cover 58 and backlight 64. In general, the backlight 64 provides light axially-outwardly (toward cover 58). This light illuminates the LCD 62 which displays any suitable computer-controlled graphics—e.g., enabling the screen 16 to function as an output device. When the user touches the coating 18 and/or cover 58, the capacitive film 60 identifies the contact or touch, as well as gestures made through the user-touch(es) indicating user commands, selections, etc.—e.g., enabling the screen 16 to function as an input device. The electronics portion 56 may comprise other layers and/or other suitable elements, the construction and operation of which will be appreciated by those skilled in the relevant art.

Light-sensitive coating 18 may be applied to an outwardly-facing side 66 of cover 58 using vapor deposition or any other suitable technique. And a thickness of the coating 18 may not substantially interfere with the input and output functions of screen 16. As used herein, a light-sensitive coating is any coating, layer, or film locating on an outermost surface of the electronics portion 56 of screen 16 which, when in the presence of light emitted from the bezel lamp 22 participates in a chemical reaction. As used herein, a chemical reaction is a process wherein at least one material of the coating 18 changes or is converted to a different substance (a different type of material). As explained more below, in at least one example, this chemical reaction may require multiple reactants (e.g., the coating 18 plus some carbon or other organic matter) to yield a new product (e.g., the different substance).

According to at least one example, the light-sensitive coating 18 comprises titanium dioxide ($TiO_2$) having any suitable thickness. According to one example, the $TiO_2$ coating 18 does not degrade, more than 10%, the transmissivity of light received by the user from the backlight 64 and further does not change, more than 5%, the capacitive response (in film 60) resulting from user-touches; however, this is merely one example, and other examples exist. In this implementation, in the presence of light from the bezel 20, the $TiO_2$ coating 18 (a reactant) plus an organic material on the surface 24 of the coating 18 (e.g., a second reactant) may yield water ($H_2O$) and carbon dioxide ($CO_2$) (the products of the chemical reaction). Titanium dioxide is merely one example of coating 18; other materials could be used instead.

Bezel 20 may include any suitable frame that extends around the periphery 54 of screen 16. Thus, in at least one example, the bezel 20 may comprise a first or upper member 70, a second or leg member 76, a third or lower member 72, and a fourth or leg member 74, wherein the upper, lower, and leg members 70-76 are coupled to one another end-to-end and have rectangular arrangement (e.g., see FIG. 4)—e.g., member 70 adjacent to member 76, member 76 adjacent to member 72, member 72 adjacent to member 74, and member 74 adjacent to member 70. Other bezel shapes are also possible—e.g., including one member examples (e.g., a curved member forming an oval or an elliptical shape in front of screen 16), and other multi-member examples (e.g., including triangular, trapezoidal, rhomboid, hexagonal, octagonal, etc. shapes), just to name a few non-limiting examples.

In one example, each member 70-76 may comprise a first or outwardly-facing face 78, 80, 82, 84 (respectively) and a second or axially-extending face 86, 88, 90, 92 (respectively). The second faces 86-92 respectively may extend axially and radially-outwardly from surface 24 of screen 16 to respective first faces 78-84. (See also FIG. 4B) showing second faces 90, 92 sloping between first faces 82, 84 respectively, and screen 16.) First faces 78-84 may be parallel to the surface 24; however, this is not required.

Figure 4:
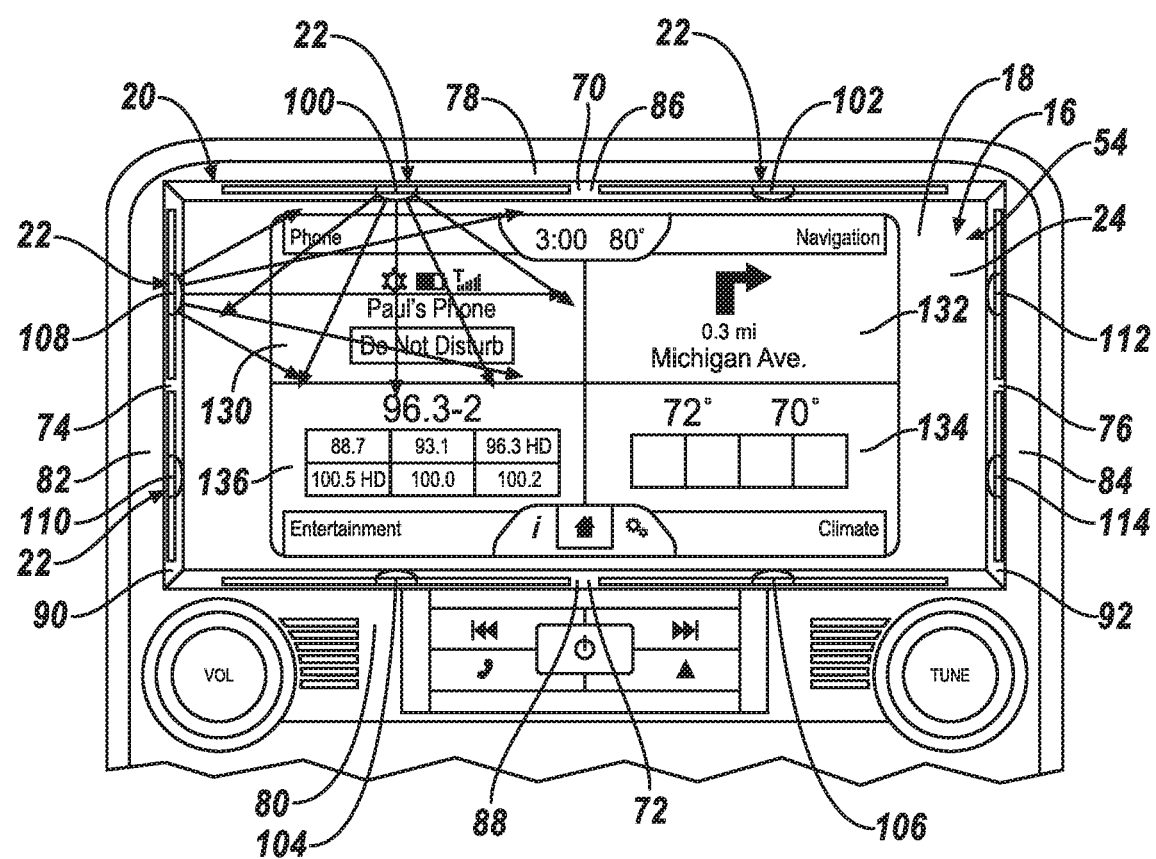
FIG. 4 is a front, schematic view of an exemplary display, illustrating a lamp in the bezel of the display comprising a plurality of light sources and graphics which divide the screen into a plurality of user-touch regions.

One or more members of bezel 20 may have a cavity 96 sized to carry lamp 22 or light source(s) thereof, as explained more below. For example, lamp 22 may comprise a plurality of light sources. For example, FIG. 4 illustrates each member 70-76 carrying a pair of light sources 100-102, 104-106, 108-110, and 112-114, respectively. Each light source 100-114 includes at least one light element and also may comprise an optic.

Figure 4A:
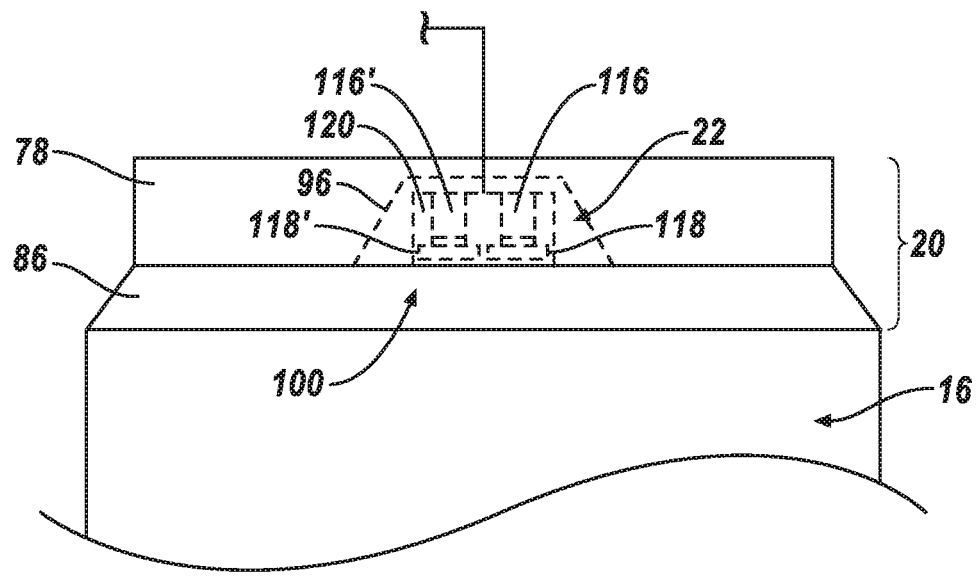
FIGS. 4A-4C are schematic diagrams of the display.
Figure 4B:
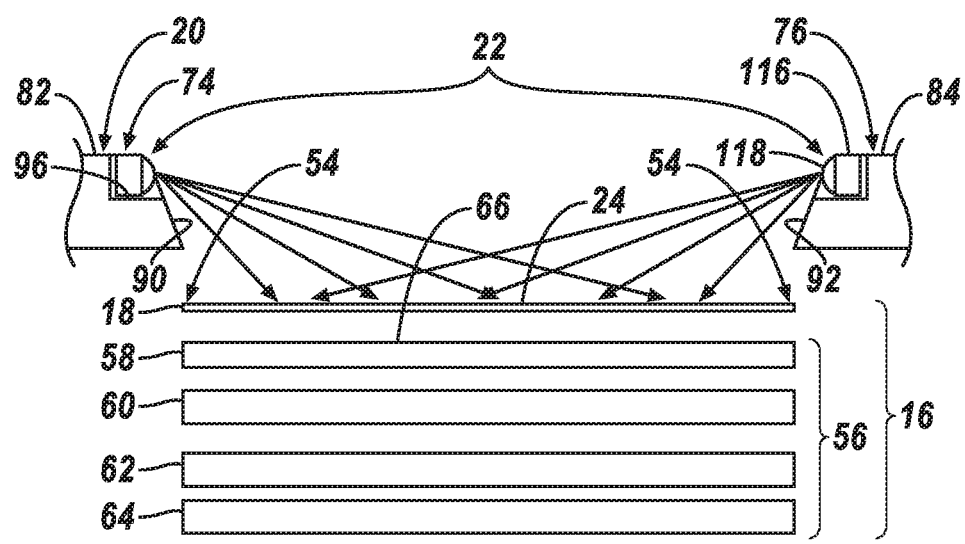

According to one example, each light source 100-114 is similar or identical; therefore, only one will be described herein. FIG. 4A illustrates a schematic view of light source 100 within cavity 96—the light source may comprise a light element 116 and optic 118 carried by a printed circuit board (PCB) 120, wherein the optic 118 is configured, as well as positioned relative to the element 116, so that light emitted from element 116 is directed toward the screen 16. As the light source 100 may be axially spaced from the screen 16, light may be directed axially inwardly from the bezel 20 toward the screen 16—i.e., light rays from the element 116 may be directed away from the cabin 36 and users therein. As will be explained more below, in at least one example, the optic 118 may direct light rays from the element 116 toward a predefined region of the screen 16.

In at least some examples, one or more of the light sources 100-114 may comprise multiple light elements. To illustrate, the light source 100 of FIG. 4A includes a second light element 116' and optic 118' carried by the PCB 120. According to at least some examples, the light elements, 116, 116' emit differing wavelengths of light. For example, element 116 may emit light in the UVA bandwidth, while element 116' may emit light in a portion of the visible bandwidth (e.g., blue or red light). Multiple light elements are not required. And element 116' and optic 118' are of course merely an example; other examples also exist.

Non-limiting examples of light elements 116 (and/or 116') include a light-emitting diode, an incandescent element, etc. Light elements 116, 116' may emit light in any suitable frequency or bandwidth, including: ultraviolet A (UVA) light of 310-390 nanometer (nm) band, UVA light centered at 365 nm, blue light (e.g., within the 400-410 nm band), red light (e.g., in the 670-700 nm band), infrared light (e.g., in 700-800 nm band), and the like. According to one example, the light power at a distance of 18 centimeters from light element 116 may be at least 1 milli-Watt per square centimeter (1 $mW/cm^2$). In other examples, the light power at a distance of 36 centimeters from light element 116 may be at least 1 $mW/cm^2$.

The optics 118, 118' may comprise any suitable optically-transmissive material having any suitable shape—e.g., it may be shaped as a lens, a prism, a waveguide, a light pipe, and the like. For example, optics 118, 118' may comprise acrylic, glass, or any other suitable material. The optics 118, 118' may be carried by the respective light elements 116, 116' (which in turn are coupled to PCB 120), or both the respective elements 116, 116' and optics 118, 118' may be coupled to PCB 120.

According to one arrangement of the bezel 20, two of light sources 100-114, when actuated, illuminate a predefined user-touch region of the screen 16. For example, screen 16 may be sub-divided into four user-touch regions 130, 132, 134, 136 (e.g., a two-by-two matrix or four quadrants of screen 16). By way of example and not limitation, region 130 may concern a user's (e.g., "Paul's") phone, region 132 may concern navigation (e.g., to the user's destination), region 134 may concern climate control settings or data, and region 136 may concern entertainment services (e.g., radio stations) available within cabin 36 (of course, any suitable quantity of user-touch regions may be used, and the input/output data displayed within the respective user-touch regions may vary). Other quantities of user-touch regions may exist in other screen examples.

During operation and use, users may touch one of regions 130-136 more than other regions (e.g., based on preference, circumstance, etc.). And as explained in greater detail below, computer 40—coupled to display 14—may count and record a quantity of user touches and/or a quantity of user-touches per region 130-136. Accordingly, an inference may be made that the regions 130-136 with the highest quantity of user-touches may be the most contaminated and in need of cleaning (or, e.g., any region having more user-touches than a predetermined threshold may be considered contaminated and in need of cleaning). Accordingly, one or more of the light sources 100-114 may be controlled selectively by computer 40 to illuminate and thereby clean the respective region of the screen 16.

According to one example, when actuated by computer 40, light source pair 108, 100 may illuminate region 130, light source pair 102, 112 may illuminate region 132, light source pair 114, 106 may illuminate region 134, and light source pair 104, 110 may illuminate region 136. According to one example, the light source 100-114 (or a pair thereof) is actuated for a predetermined period of time to activate coating 18. For example, where the coating 18 is $TiO_2$, the respective light source(s) may be actuated for a period of ten minutes thereby causing a chemical reaction to occur at the surface 24 of the $TiO_2$ coating for a duration of at least two hours. In examples having multiple light elements, the illumination period for an element emitting UVA light (e.g., element 116) may be a predetermined period of time, whereas the illumination period for other elements (e.g., element 116') which are not emitting UVA light or the like may not be limited or may have a different duration.

By way of example only, one reaction with the light-sensitive coating 18 is described. When UVA light is directed from lamp 22 to surface 24, it can kill living organic matter (e.g., germs such as bacteria, viruses, etc.). When the UVA light has a minimum threshold energy at the point of incidence (at surface 24), electrons are released from the $TiO^2$ coating 18. These electrons can combine with water molecules in the air resulting in hydroxyl radicals (OH)—an uncharged form of hydroxide ions ($OH^-$). The hydroxyl radicals can combine with organic matter breaking apart the organic matter's chemical bonds, yielding water ($H_2O$) and carbon dioxide ($CO_2$). Accordingly, organic matter on screen 16 is not only killed, but removed therefrom (e.g., effectively carried away by the water and carbon dioxide molecules)—e.g., leaving surface 24 clear of user-contact or user-touch contaminants such as user bodily fluids. The chemical reaction caused by the light from lamp 22 and coating 18 on screen 16 thus inhibits the dissemination of germs—and can even have a deodorizing effect on the surrounding air.

According to one example, computer 40 may inhibit—at least temporarily—actuation of light sources 100-114 based on one or more predetermined criteria, as also explained in greater detail below (FIGS. 5-8). For example, even though computer 40 may determine that a timer associated with cleaning surface 24 has expired (or even though computer 40 may determine that the surface 24 has been touched a predetermined quantity of times since its last cleaning), computer 40 may delay actuation of light sources 100-114 to minimize user exposure to UVA or similar light. For example, computer 40 may delay actuation: (a) when computer 34 determines an occupant is in cabin 36 and when a light detection sensor 140 (FIG. 3) indicates ambient light is less than a threshold; or (b) when computer 34 determines that an occupant is in cabin 36, sensor 140 indicates ambient light greater than the threshold, and computer 38 indicates that the transmission is not in PARK. Other delay examples also exist—e.g., including those described in greater detail below.

As used herein, a light detection sensor 140 may provide any suitable wired or wireless output to computer 40 indicating a quantity of light; e.g., this may include triggering based on a predetermined quantity of ambient light (and then sending an indication of that the sensor 140 has been triggered), and/or it may include providing a range of electrical values that correspond to different levels of ambient light—thereby permitting computer 40 determine a corresponding luminance value. As used herein, ambient light is light within the cabin 36 of vehicle 12; this may include direct or diffused sunlight which enters the cabin 36 via windows, ports, sunroofs, etc. which may be in the open or closed position.

According to another example, the computer 40 can be triggered to selectively actuate one or more of light sources 100-114 via a switch 142 (FIG. 3). This switch may be part of display 14, or it may be located elsewhere. In at least some examples, a vehicle technician uses switch 142 to clean the display or perform other maintenance tasks.

Figure 4C:
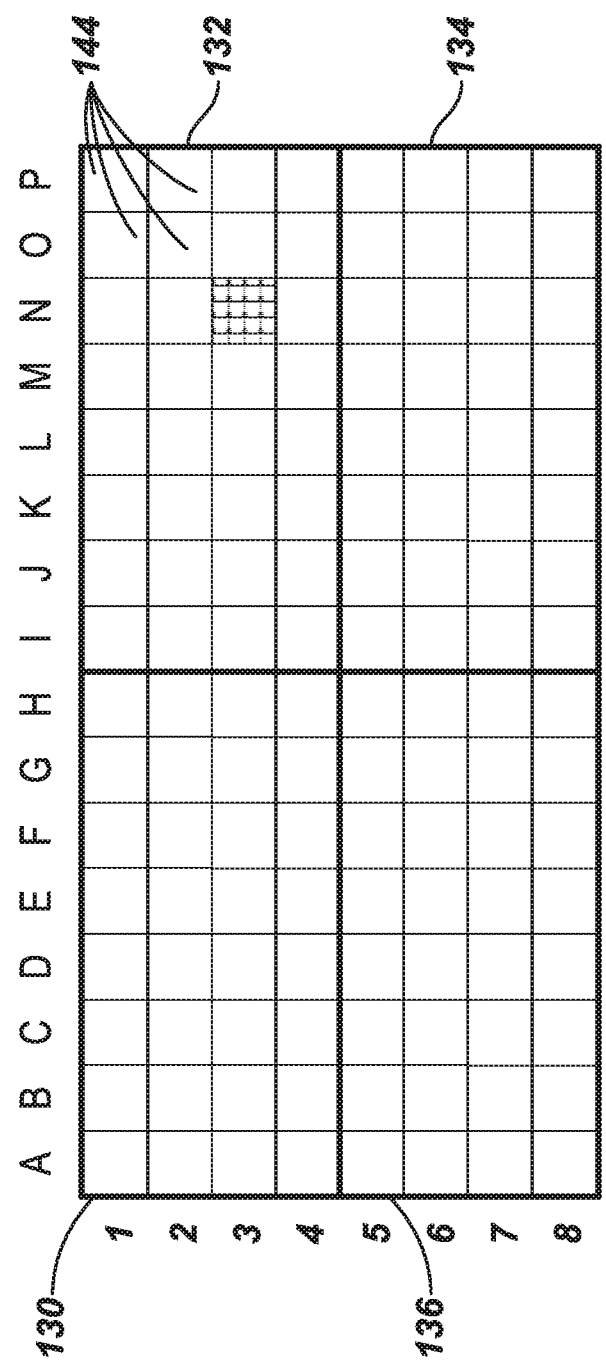
Figure 5:
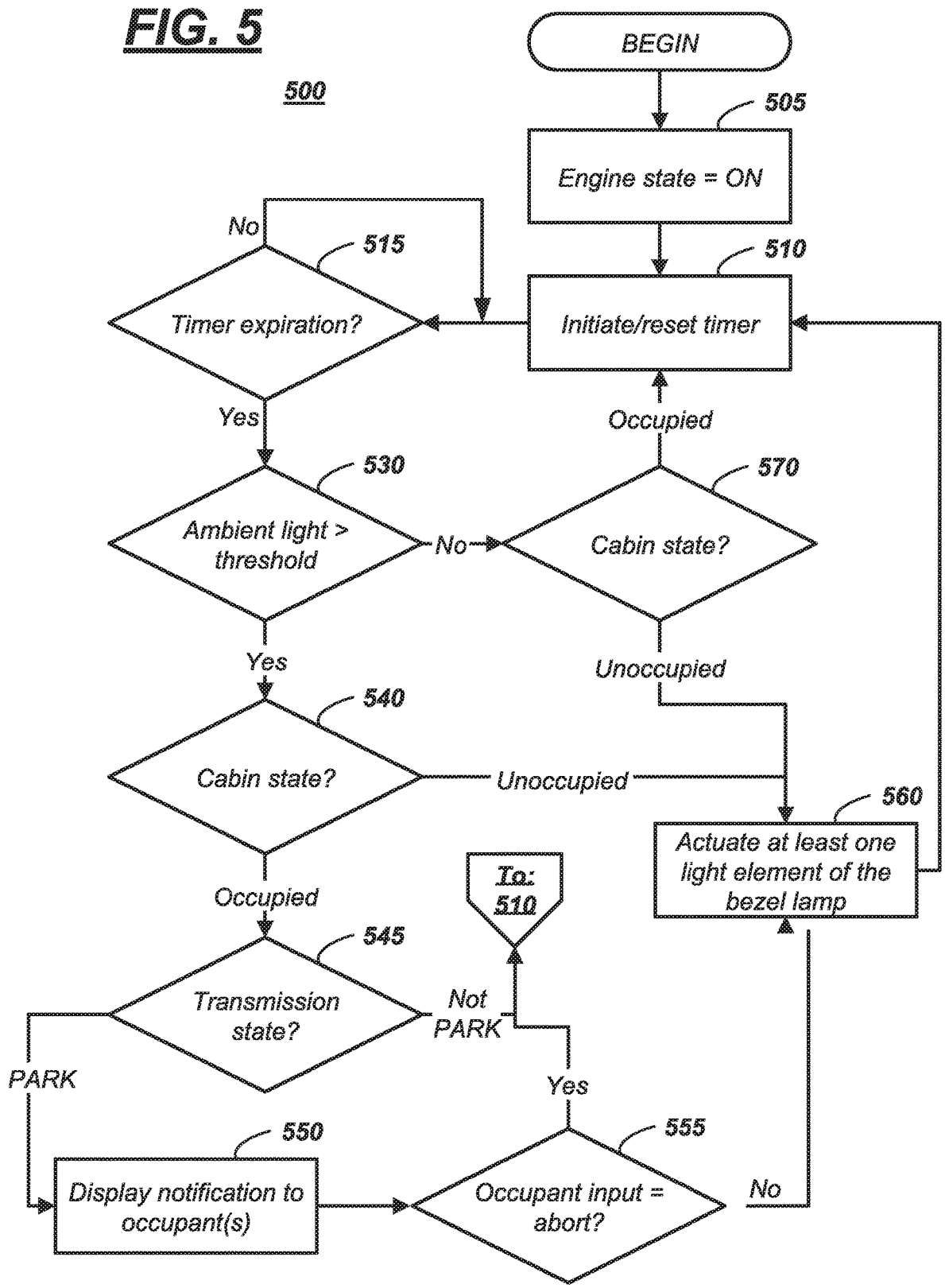
FIGS. 5-8 are flow diagrams illustrating various processes to clean and/or illuminate the vehicle display, which may be executed by a computer of the interior cleaning system.

According to another example, which is explained in greater detail below, the screen 16 may be divided into different regions—instead of or in addition to regions 130-136. FIG. 4C illustrates one example wherein screen 16 is divided into a number of finger contact regions 144. In this illustration, the screen is divided into a sixteen-by-eight array of regions 144 (e.g., comprising one hundred-and-twenty-eight contact regions 144); however, this is merely an example. In at least one example, the size of the regions 144 approximate the size of a human touch or fingerprint. For explanatory purposes herein, the regions 144 horizontally are labeled A, B, C, . . . , P and vertically are labeled 1, 2, 3, . . . , 8.

Some touchscreens react to electrical energy carried by the human fingertip. Consequently, when the film 60 perceives a user-touch, it is really perceiving an increase in electrical charge on screen 16. However, frequent contact with human skin can cause the touchscreen to behave abnormally when determining selections, gestures, commands, etc. For example, in capacitive touchscreen implementations, this may occur in part due to a build-up of contaminants (e.g., such as human bodily fluids or the like) on surface 24 which retain electrical charge deposited there by the user-touches. More particularly, one or more capacitive circuits within the capacitive film 60 may measure a higher than nominal surface charge which is really due to the presence of the contaminant on surface 24, not a user-touch. Such erroneous touch-determinations can result in the display 14 determining user selections or commands which were not intended by the user—resulting in user frustration.

As described more below, computer 40 may determine a local differential capacitance between one or more regions 144 and respective neighboring regions 144. For example, in FIG. 4C, computer 40 may determine that a capacitance value of a first region 144 (e.g., labeled N3) is a threshold larger than its neighboring regions 144 (labeled M2, N2, O2, M3, O3, M4, N4, O4). According to one example, the computer 40 determines an erroneous touch-determination by determining that the respective region (N3) has a capacitance larger than a threshold for a predetermined period of time (e.g., longer than 10 seconds). For example, an inference may be that if the region 144 (N3) has the threshold capacitance for more than 10 seconds, it is contaminated. That is, the inference may include: a user is unlikely to hold his/her finger to the screen 16 in that location for more than 10 seconds. This of course is one way to determine that surface 24 has contaminants and needs to be purged; other techniques may be employed as well. Further, ten seconds is merely an example; other values may be used.

As described above, different types of light elements may be used (e.g., 116, 116'). In some examples, element 116 may emit UVA light, while element 116' concurrently may emit light in another wavelength (e.g., red light, blue light, etc.). For example, certain light wavelengths are known to best visually illuminate blood, semen, saliva, etc. According to one example, the computer 40 may actuate elements 116' (e.g., 415 nm) to illuminate contaminants (e.g., blood) on the surface 24 of screen 16 (e.g., to show the user whether the screen 16 is clean or contaminated), and then use elements 116 (e.g., 365 nm) to clean the surface 24, as described above.

Turning now to FIGS. 5-8, examples of computer-implemented processes 500, 600, 700, 800 of cleaning display 14 are shown. Computer 40 may be programmed to execute one or more of these processes independently, at least partially concurrently, in combination with one another etc.

Process 500 (FIG. 5) illustrates a set of instructions executable by computer 40 to purge screen 16 according to a cleaning schedule. For example, consider again the autonomous-taxi example set forth above—here, vehicle 12 may be used repeatedly throughout the day and/or evening hours to move different users to their respective destinations. Consequently, many users may use vehicle cabin 36, and many different users may touch the screen 16. According to process 500, the screen may be cleaned regularly (e.g., throughout the period of use).

Process 500 may begin with block 505, wherein the engine state is ON. Computer 40 may detect this, or e.g., computer 40 may be in an OFF state until vehicle is powered ON. Hence, if computer 40 is ON, it may be inferred that the engine state is ON. In at least one example, computer 40 receives an electrical signal via network connection 50 from computer 38 of powertrain system 32 indicating that the engine state is ON.

In block 510 which follows, computer 40 may initiate (or reset) a timer. The timer may measure a predetermined interval of time. For example, the interval may be approximately two hours (or some other suitable value). In at least one example, a duration of the interval corresponds to an activated time period of the light-sensitive coating 18. According to one example, it has been determined that when light (within a 310-390 nm wavelength) contacts the surface 24 (e.g., comprising a $TiO_2$ coating 18) for an activated time period of ten minutes, having an incident energy of at least 1 $mW/cm^2$, then the coating 18 will undergo chemical reactions with the organic matter on surface 24 for the next two hours. Hence, when the duration of the interval (e.g., 2 hours) corresponds to the activated time period of the light-sensitive coating 18 (e.g., 2 hours), then surface 24 may be repeatedly and/or continually cleaned or purged from contaminants. The timer may be implemented in software and/or using discrete electrical components coupled to the processor 42.

In block 515 which follows, computer 40 may determine whether the timer has expired. When the timer has not expired, the process 500 may loop back and repeat block 515 until the timer does expire. When the timer has expired, process 500 may proceed to block 530.

In block 530, computer 40 may determine—using sensor 140—whether the ambient light (e.g., in cabin 36) is greater than a threshold. According to one example, the threshold may be 500 lux (e.g., wherein 1 lux=1 lumen/$meter^2$). Other threshold examples include: 100 lux, 300 lux, and 400 lux, just to name a few. Thus, in block 530, when the ambient light detected by sensor 140 is greater than the threshold, the process proceeds to block 540; and when the ambient light is determined to be not greater than the threshold, then the process proceeds to block 570. According to at least one example (e.g., wherein UVA light is emitted from at least one of the elements 116, 116' of lamp 22), the ambient light threshold value corresponds to an average-user pupil dilation. For example, when ambient light is greater than the threshold, the average user's pupil will be less dilated—and consequently less sensitive to the low-levels of UVA light emitted by lamp 22.

In block 540, computer 40 may determine the cabin state (e.g., an occupied state or an unoccupied state). For example, computer 40 may receive an indication of the cabin state via network connection 50 from computer 34 of occupancy detection system 30. When computer 40 determines that the cabin state is occupied, process 500 may proceed to block 545. And when the computer 40 determines that the cabin state is unoccupied, the process can proceed to block 560.

In block 545, computer 40 may determine the state of the vehicle transmission—e.g., again receiving data from computer 38. Vehicle transmission states can include: PARK, DRIVE, REVERSE, NEUTRAL, etc. When computer 40 determines the state to be PARK, then process 500 may proceed to block 550; if any other state is determined, in at least one example, the process proceeds to block 510 (e.g., resetting the timer) and re-initiating at least a portion of process 500. In this latter instance, the relative state and attentiveness of the users in the vehicle 12 may be unknown, and thus, computer 40 may determine to attempt to purge the screen 16 of contaminants following a subsequent interval of the timer.

Blocks 550 and 555 are optional (e.g., in implementations where they are omitted, process 500 may proceed directly to block 560). In block 550, via display 14, computer 40 may notify the users of the intended actuation of lamp 22. For example, as explained in block 555 which follows, the users may be given the opportunity to opt 'out' of being in the cabin 36 while the screen 16 is purged.

In block 555, computer 40 may determine whether an input from the occupant is to abort the purging or cleaning of screen 16. For example, computer 40 may determine whether an input is received via display 14 (e.g., a touch-screen input)—e.g., indicating that the user does not wish to permit the screen 16 to be purged while he/she occupies the vehicle 12. If an abort indication is received, process 500 may proceed to block 510 and re-initiate at least a portion of process 500. And if the input indicates the user's desire to clean screen 16 (or if no indication is received), then the process may proceed to block 560.

In block 560, computer 40 may actuate at least one light element 116, 116', etc. According to one example, the computer 40 actuates a light element that emits light in the UVA band. This light, being directed at screen 16, impinges upon the surface 24 killing living organic matter (e.g., including bacteria and viruses), and causes a chemical reaction with light-sensitive coating 18 (e.g., effectively carrying away carbon-based matter), as described above.

Block 560 may include various lamp illumination techniques. According to one example, all light sources 100-114 may be actuated. In one example, the orientation of light from these sources 100-114 collectively impinge upon the entirety of surface 24.

According to another example, computer 40 selectively actuates light sources 100-114, as described above. For example, light sources 108 and 100 are actuated to purge user-touch region 130. Or light sources 102 and 112 are actuated to purge user-touch region 132. Or light sources 114 and 106 are actuated to purge user-touch region 134. Or light sources 104 and 110 are actuated to purge user-touch region 136. Or for example, any suitable combination of regions 130-136 are purged concurrently. In at least one example, these light source pairings (e.g., 108,100; 102, 112; 114, 106; and 104, 110) may emit light directed respective regions 130, 132, 134, and 136 with less than 10% overlap into the non-targeted region.

In other examples, one or more light sources (or even light elements 116, 116') could be used to purge finger contact regions 144 or the like—e.g., a plurality of light elements 116, 116' could be oriented at different regions 144 or adjacent groupings of regions 144 so that when the respective light source or respective light element is actuated, only the region 144 or grouping of regions 144 is purged. Still other examples exist. As described above, block 560 may occur for a predetermined activated time period (e.g., such as ten minutes or the like); in other examples, the activated time period may be shorter or longer. Following block 560, the process may loop back to block 510 and re-initiate at least a portion of process 500.

Returning to block 570 (which may follow block 530 when the ambient light is not greater than the threshold), in block 570, the cabin state may be determined according to a procedure similar or identical to that described in block 540. For example, in block 570, computer 40 may receive an indication from computer 34 whether the cabin 36 is in an occupied state or an unoccupied state. If in block 570 the computer 40 determines that the cabin state is unoccupied, then the process may proceed to block 560 (and computer 40 may actuate at least one light source or one light element, as described above). However, if in block 570 the computer 40 determines that the cabin state is occupied, then the process may proceed to block 510 and re-initiate at least a portion of process 500. In this latter instance, it may not be desirable to illuminate the screen 16 using, e.g., UVA light, when the user's pupils may be more sensitive thereto (e.g., due to low cabin lighting conditions), as described above.

Returning to block 540, as described above, when the cabin state is unoccupied, process 500 may proceed to block 560. Here again, following block 540, computer 40 may actuate at least one respective light source or respective light element, as described above. And thereafter, the process may loop back to block 510 and re-initiate at least a portion of process 500.

Figure 6:
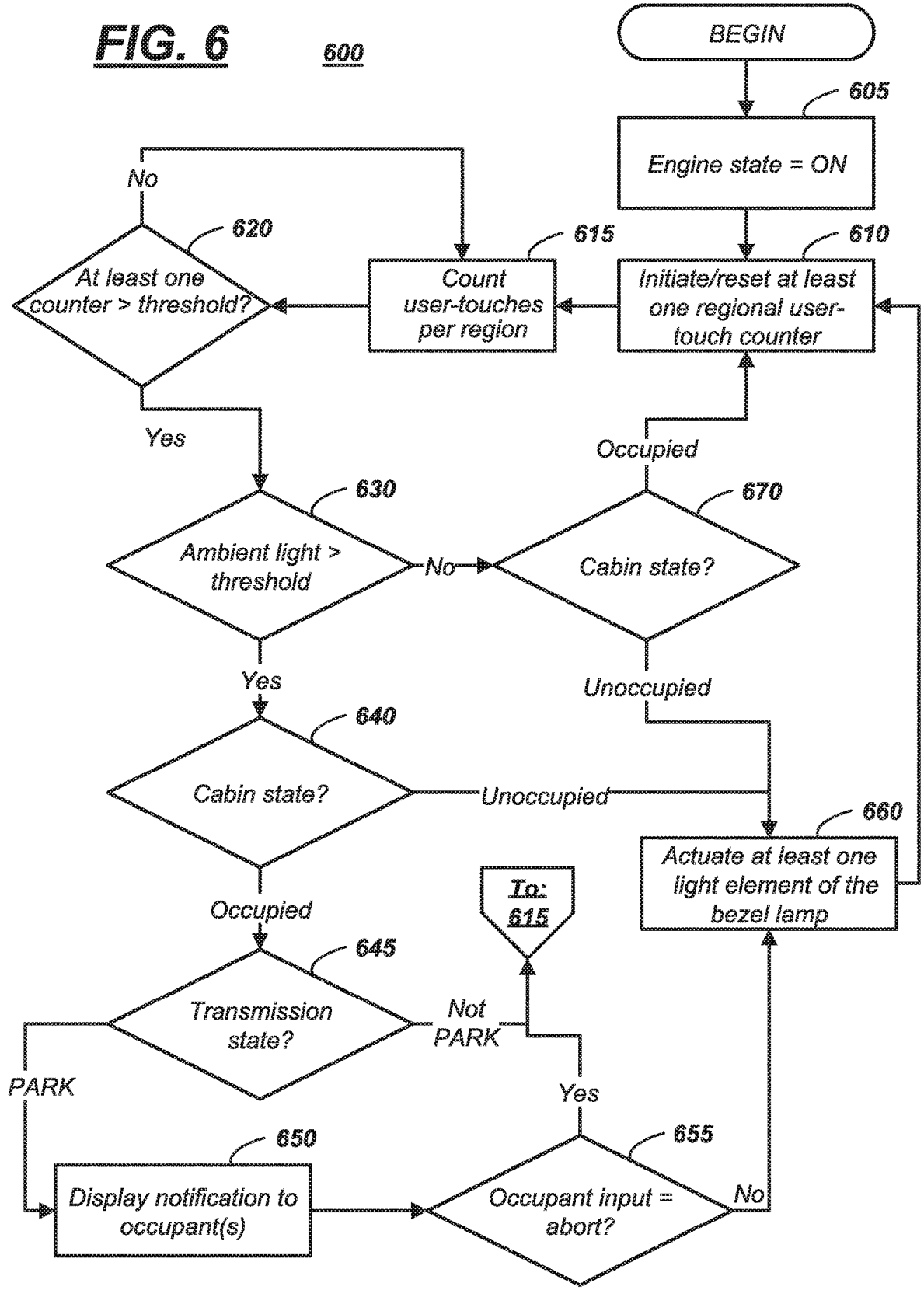

Turning now to FIG. 6, process 600 illustrates a set of instructions executable by computer 40 to purge screen 16 based on a quantity of user-touches per user-touch region 130-136. For example, consider again that certain regions 130-136 may be touched more often by users than others. The efficiency of purging the display 14 may be improved by cleaning those regions 130-136 (or other similarly-arranged regions) based on a quantity of user-touches, rather than simply cleaning the entire screen 16 during each purge.

Process 600 begins with block 605. Block 605 may be similar or identical to block 505 (previously described). Therefore, it will not be re-described here.

Block 610, which follows block 605, may comprise initiating (or resetting) at least one regional user-touch counter. Consider four regions 130, 132, 134, 136 as merely one example of a plurality of user-touch regions. In this instance, computer 40 may initiate four counters—one for each respective region 130-136. As described below, each time a user touches the screen 16 in the respective region 130-136, the respective counter may be incremented.

In block 615 which follows, computer 40 determines a user-touch of screen 16, and computer 40 increments at least one of the counters. For example, if the user-touch is determined in region 136, then the respective counter for region 136 is incremented.

Block 620 follows block 615. In block 620, the computer 40 determines whether the any of the counters have exceeded a predetermined threshold of user-touches. For example, the threshold may be 30 user-touches, 50 user-touches, 100 user-touches, etc., just to cite a few non-limiting examples. Continuing with the example above, computer 40 may determine whether the latest user-touch (e.g., to region 136) has caused the respective counter for that region to exceed the threshold. If the respective counter has exceeded the threshold, then the process proceeds to block 630. If the respective counter (as well as the other counters) have not exceeded the threshold, then process 600 loops back and repeats block 615. Process 600 may loop back any suitable quantity of times as it increments the respective counters. Further, process 600 may proceed to block 630 (e.g., for region 136) while concurrently looping back and counting user-touches of regions 130-134.

According to one example, each user-touch increments the counter by one. However, according to one non-limiting example, a single user-touch may not always increment the counter by one. For example, when multiple user-touches occur within a predetermined touch-interval, then the first user-touch may be counted as one, while subsequent user-touches may be counted as a portion of one count (e.g., one-half of a count or the like). For example, the amount of bodily fluid transferred to the screen 16 by the first user-touch verses the second user-touch may vary. For example, a majority of the user's skin oils may be transferred to surface 24 during the first user-touch, whereas less than a majority of the skin oils may be transferred to surface 24 during a rapid subsequent user-touch.

To illustrate, consider a user touching region 136 two times within a touch-interval of 1.5 seconds. Computer 40 may increment the respective counter by one for first user-touch and by one-half for each subsequent user-touch. Consequently, these two user-touches will increment the counter in total only one-and-one-half user-touches. A touch-interval of 1.5 seconds is merely an example. Further, other touch-interval durations could be used as well (e.g., 2 seconds, 3 seconds, etc.).

Blocks 630, 640, 645, 650, 655, 660, and 670 may be similar or identical to respective blocks 530, 540, 545, 550, 555, 560, and 570. Thus, these will not be re-described here. However, it should be appreciated that in block 660, the actuation of the at least one respective light source or respective light element may be a light source or element which directs light on the respective user-touch region which exceeded the threshold in block 620. Continuing with the example above, where the counter associated with user-touch region 136 exceeded the threshold, light sources 104 and/or 110 may be actuated onto the surface 24 within region 136 (and in at least one example, both 104, 110 are actuated).

Figure 7:
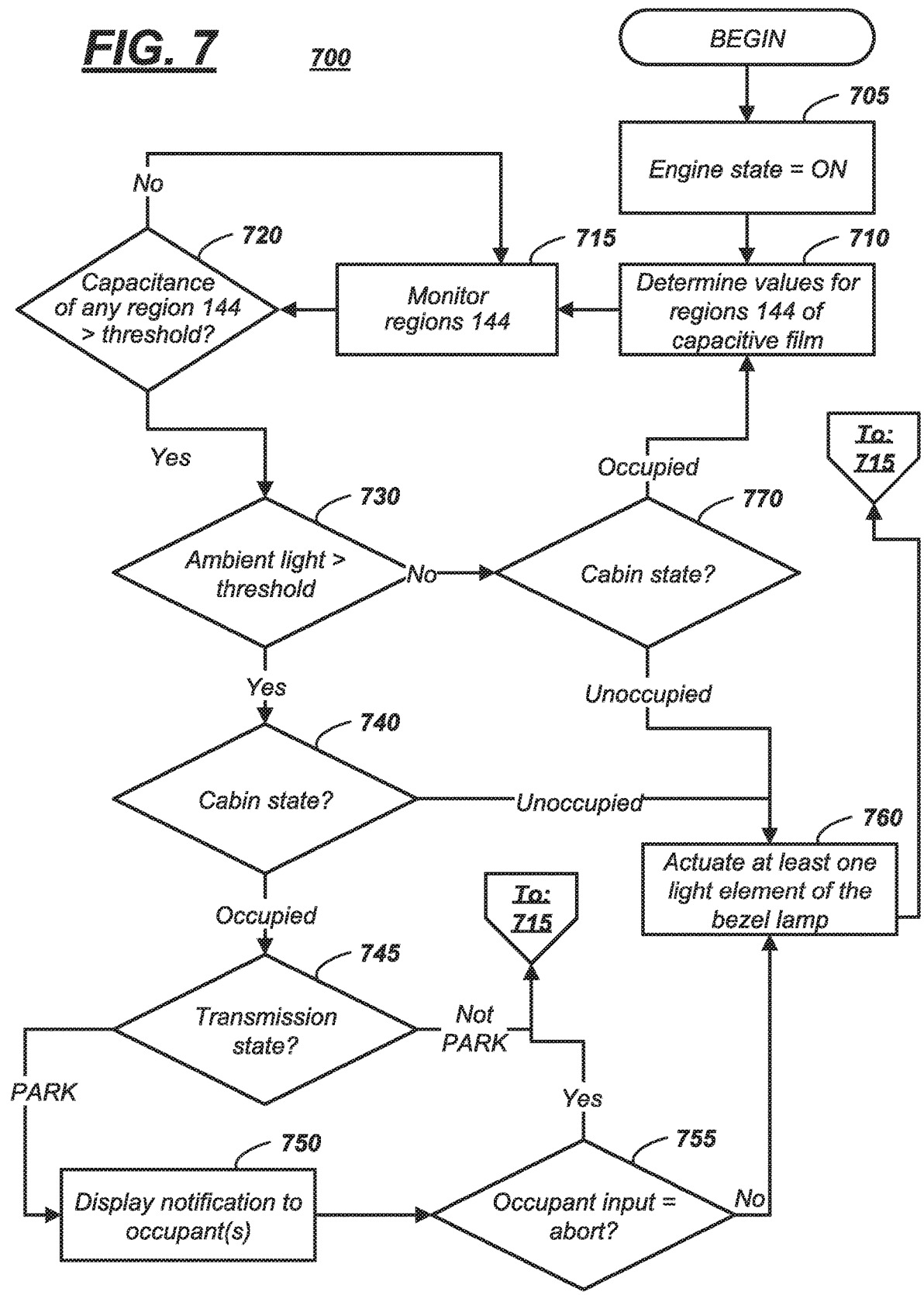

Turning now to FIG. 7, process 700 illustrates a set of instructions executable by computer 40 to purge screen 16 based on a differential capacitance of finger contact regions. For example, consider that certain regions 144 may experience a build-up of contaminants based on human contact, as described above and that some capacitive circuits may make erroneous touch-determinations based on such contaminant build-up. Process 700 illustrates an example of computer 40 detecting and purging such regions 144.

Process 700 begins with block 705. Block 705 may be similar or identical to block 505 (previously described). Therefore, it will not be re-described here.

In block 710, which follows block 705, computer 40 may determine baseline capacitance values for finger contact regions 144 associated with film 60. For example, it may be expected that a region 144 of the surface 24 (which corresponds with the capacitive circuit therebelow (in film 60)) may carry a nominal static surface charge. Thus, block 710 may determine a baseline value for all regions 144 using historical charge data associated with the screen 16. In other examples, this characteristic may be stored in memory 44 (e.g., a preconfigured value). As will be described more below, when the corresponding capacitive circuit determines a value of a contact region 144 that is greater than this baseline value, then the computer 40 may determine a user-touch has occurred or that the region 144 is contaminated.

In block 715 which follows, computer 40 monitors the capacitive values of the contact regions 144 and compares these values with the baseline value determined in block 710. Block 720 follows block 715.

In block 720, the computer 40 determines whether the capacitive values of any of regions 144 is greater than a threshold (e.g., than the baseline value or a value a predetermined amount larger than the baseline value). Block 720 further may determine whether the respective capacitive value is larger than the threshold for a predetermined period of time (e.g., longer than 10 seconds or the like). If the capacitive value of any respective region 144 exceeds the threshold for the predetermined period of time, then process 700 proceeds to block 730. If none do, then the process loops back and repeats block 715.

During the execution of blocks 705-720, it should be appreciated that screen 16 may be purged using the techniques described above for other reasons (e.g., see processes 500, 600, 800, for example)—thereby removing build-up contaminants before process 700 proceeds to block 730. An in at least one other example, process 700 may facilitate cleaning the screen 16 during times when processes 500 and/or 600 were aborted (e.g., due to user preference to clean the screen 16 at a later time).

Blocks 730, 740, 745, 750, 755, 760, and 770 may be similar or identical to respective blocks 530, 540, 545, 550, 555, 560, and 570. Thus, these will not be re-described here. However, it should be appreciated that in block 760, the actuation of the at least one respective light source or respective light element may be a light source or element which directs light on the respective user-touch region which exceeded the threshold in block 720, or even at the respective contact region 144 (or grouping of contact regions 144) determined in block 720.

Figure 8:
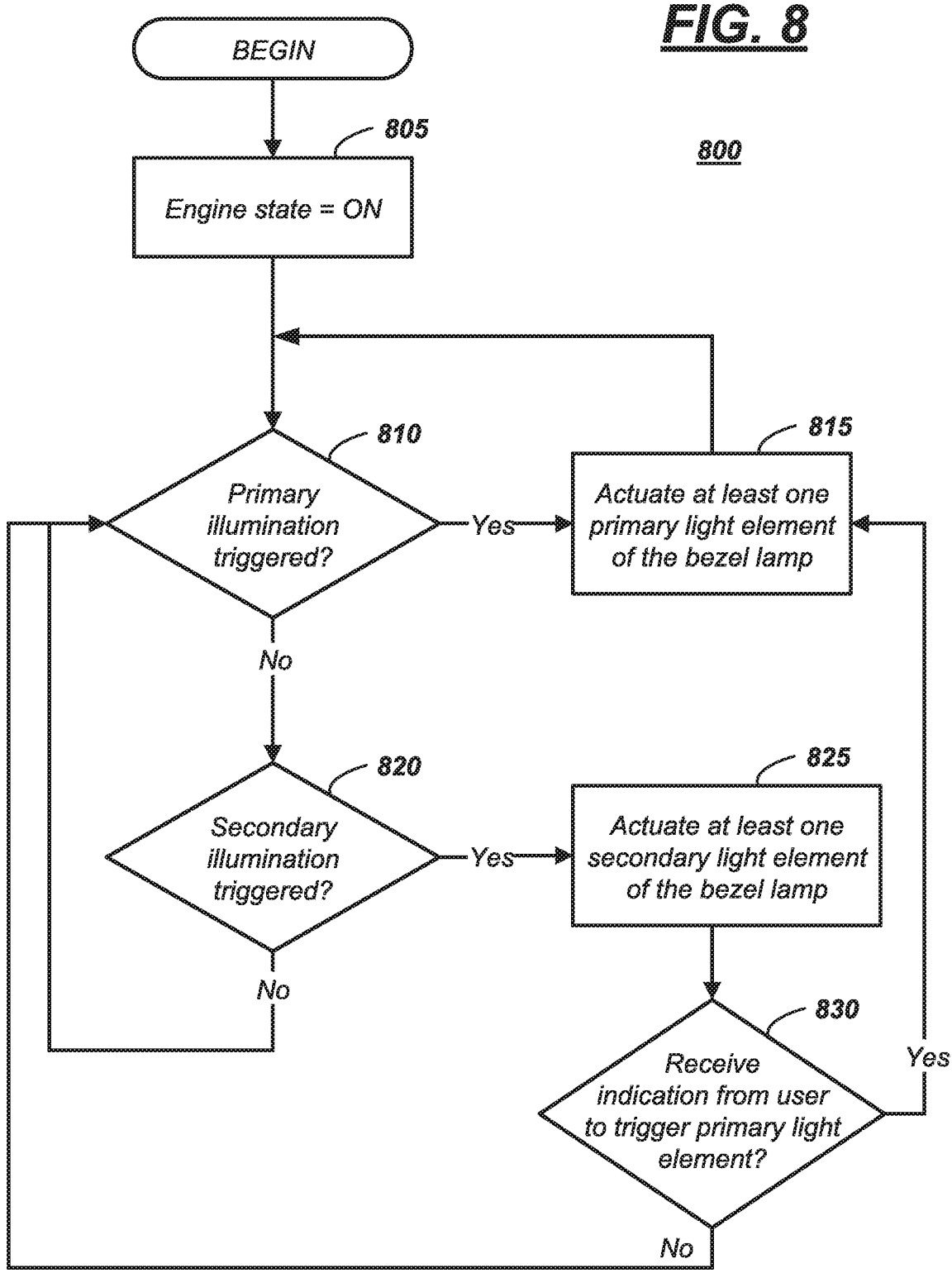

Turning now to FIG. 8, process 800 illustrates another example of computer 40 purging screen 16 of display 14. Process 800 begins with block 805. Block 805 may be similar or identical to block 505 (previously described). Therefore, it will not be re-described here.

Block 810 which follows may include computer 40 determining whether a primary illumination is triggered. As used herein, a primary illumination is an actuation of at least one light source of lamp 22 that emits light in the UVA band. For example, the user (e.g., which may include authorized service personnel) may manually actuate the lamp 22 (or light sources or elements thereof) via switch 142. As described above, this switch 142 may actuate all or a portion of light sources 100-114, and/or any of light elements 116, 116'.

If the primary illumination is triggered, the process proceeds to block 815 and illuminates at least one of the primary light elements 116, 116' of a respective light source—thereby emitting UVA light. Following block 815, the process may loop back to block 810.

If the primary illumination of screen 16 is not triggered, then process 800 proceeds to block 820. In block 820, computer 40 may determine whether a secondary illumination is triggered. As used herein, a secondary illumination is an actuation of at least one light source of lamp 22 that emits light in a band other than the UVA band. Again, a user may trigger this actuation for a variety of reasons—e.g., including wishing to see whether contaminants are on the screen 16. As discussed above, visible light (e.g., red light, blue light, etc.) may be used to better identify some types of contaminants on surface 24, as will be appreciated by those skilled in the art, and the secondary illumination may outline or otherwise distinguish these contaminants.

If the secondary illumination is triggered, the process proceeds to block 825 and illuminates at least one of the secondary light elements 116, 116' of a respective light source—thereby emitting light other than UVA light. Following block 825, the process may proceed to block 830.

In block 830, after having attempted to visibly illuminate contaminants on the screen 16, the computer may determine again whether the user wishes now to purge the contaminants therefrom. For example, the computer 40 could instruct the display 14 to provide a notification to the user to actuate purging of the screen 16. If in block 830, the computer 40 receives an indication from the user to trigger the primary illumination, process 800 proceeds to block 815 (actuating at least one light source or light element. Thereafter, the process loops back to block 810, as described above. And if in block 830, the computer 40 receives no indication from the user to trigger the primary illumination, process 800 may proceed directly to block 810 (described above).

Any of processes 500, 600, 700, 800 may be used at least partially concurrently with one another. Again, these processes are merely examples of ways to detect and/or purge the screen 16 of contaminants; still other examples exist. For example, the computer 40 may determine to actuate one or more light sources or light elements based on the cabin 36 being unoccupied—e.g., without determining other criteria (e.g., ambient lighting, timer expirations, thresholds exceeded, etc.).

Thus, there has been described an interior cleaning system for a vehicle. The system includes a display having a screen with a light-sensitive coating and a bezel that includes a lamp. The lamp is arranged to direct light toward the screen. In some examples, light from the lamp includes light in the ultraviolet band that activates the coating to clean the surface thereof. The system further may comprise a computer that controls when to emit light that activates the light-sensitive coating.

In general, the computing systems and/or devices described may employ any of a number of computer operating systems, including, but by no means limited to, versions and/or varieties of the Ford SYNC® application, AppLink/Smart Device Link middleware, the Microsoft® Automotive operating system, the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX and iOS operating systems distributed by Apple Inc. of Cupertino, Calif., the BlackBerry OS distributed by Blackberry, Ltd. of Waterloo, Canada, and the Android operating system developed by Google, Inc. and the Open Handset Alliance, or the QNX® CAR Platform for Infotainment offered by QNX Software Systems. Examples of computing devices include, without limitation, an on-board vehicle computer, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The processor is implemented via circuits, chips, or other electronic component and may include one or more microcontrollers, one or more field programmable gate arrays (FPGAs), one or more application specific circuits ASICs), one or more digital signal processors (DSPs), one or more customer integrated circuits, etc. The processor may be programmed to process the sensor data. Processing the data may include processing the video feed or other data stream captured by the sensors to determine the roadway lane of the host vehicle and the presence of any target vehicles. As described below, the processor instructs vehicle components to actuate in accordance with the sensor data. The processor may be incorporated into a controller, e.g., an autonomous mode controller.

The memory (or data storage device) is implemented via circuits, chips or other electronic components and can include one or more of read only memory (ROM), random access memory (RAM), flash memory, electrically programmable memory (EPROM), electrically programmable and erasable memory (EEPROM), embedded MultiMediaCard (eMMC), a hard drive, or any volatile or non-volatile media etc. The memory may store data collected from sensors.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A system, comprising:
 a display, comprising:
  a screen comprising a cover comprising a light-sensitive coating, wherein the cover comprises a first predefined region and a second, different predefined region;
  a bezel extending outwardly from the screen and forming at least a portion of a periphery of the screen; and
  a lamp carried by the bezel and comprising a first light source and a second light source, wherein light from the first and second light sources is directed axially and radially-inwardly from the bezel and toward the cover, wherein light from the first light source is directed to the first predefined region and wherein light from the second light source is directed to the second predefined region; and
 a computer, comprising:
  a processor; and
  memory storing instructions executable by the processor, the instructions comprising to:
   (a) determine that a vehicle cabin is in an occupied state;
   (b) determine that an ambient light in the cabin is greater than a first threshold;
   (c) determine at least one predetermined criteria, wherein the at least one predetermined criteria includes that a state of a transmission is in PARK; and
   (d) based on the determining (a), (b), and (c), actuate at least the first light source or the second light source to activate the light-sensitive coating on the respective first or second predefined region.

2. The system of claim 1, wherein the at least one predetermined criteria is an expiration of a timer associated with a last cleaning of the screen.

3. The system of claim 1, wherein the at least one predetermined criteria is a predetermined quantity of user-touches of the screen since a last cleaning of the screen.

4. The system of claim 3, wherein the system further comprises a counter, wherein the predetermined quantity of user-touches comprises a first user-touch and a second user-touch, wherein the instructions further comprise to:
 determine that the first user-touch and the second user-touch occur within a predetermined touch-interval; and
 in response thereto, count the second user-touch as less than one incrementation of the counter.

5. The system of claim 1, wherein the at least one predetermined criteria is a predetermined quantity of user touches of either the first or second predefined region since a last cleaning of the screen.

6. The system of claim 1, wherein the at least one predetermined criteria comprises determining that a contact region of the screen—within one of the first or second predefined regions—maintains a surface charge that is greater than a second threshold for at least a predetermined period of time.

7. The system of claim 1, wherein the coating comprises titanium dioxide (TiO$_2$), wherein the lamp emits light at a wavelength within 310-390 nanometers (nm).

8. The system of claim 1, wherein the at least one predetermined criteria includes failing to receive an input to abort the actuating (d) in response to a notification of an intent to perform the actuating (d) sent upon determining that the state of the transmission is in PARK.

9. A system, comprising:
a display, comprising:
  a screen comprising a cover comprising a light-sensitive coating, wherein the cover comprises a first predefined region and a second, different predefined region;
  a bezel extending outwardly from the screen and forming at least a portion of a periphery of the screen; and
  a lamp carried by the bezel and comprising a first light source and a second light source, wherein light from the first and second light sources is directed axially and radially-inwardly from the bezel and toward the cover, wherein light from the first light source is directed to the first predefined region and wherein light from the second light source is directed to the second predefined region; and
a computer, comprising:
  a processor; and
  memory storing instructions executable by the processor, the instructions comprising to:
    (a) determine whether a vehicle cabin is in an occupied state;
    (b) determine at least one predetermined criteria, wherein the at least one predetermined criteria includes that a state of a transmission is in PARK; and
    (c) based on the determinations of (a) or (b), actuate at least the first light source or the second light source to activate the light-sensitive coating on the respective first or second predefined region.

10. The system of claim 9, wherein the coating comprises titanium dioxide (TiO$_2$), wherein the lamp emits light at a wavelength within 310-390 nanometers (nm).

11. The system of claim 9, wherein the at least one predetermined criteria comprises determining that an ambient light within the cabin exceeds a threshold.

12. The system of claim 9, wherein the at least one predetermined criteria comprises an expiration of a predetermined interval of time, wherein the instructions further comprise to use a timer to measure the predetermined interval of time.

13. The system of claim 9, wherein the at least one predetermined criteria is a predetermined quantity of user-touches of the screen since a last cleaning of the screen.

14. The system of claim 13, wherein the system further comprises a counter, wherein the predetermined quantity of user-touches comprises a first user-touch and a second user-touch, wherein the instructions further comprise to:
  determine that the first user-touch and the second user-touch occur within a predetermined touch-interval; and
  in response thereto, count the second user-touch as less than one incrementation of the counter.

15. The system of claim 9, wherein the at least one predetermined criteria is a predetermined quantity of user touches of either the first or second predefined region since a last cleaning of the screen.

16. The system of claim 9, wherein the at least one predetermined criteria comprises determining that a contact region of the screen—within one of the first or second predefined regions—maintains a surface charge that is greater than a threshold for at least a predetermined period of time.

17. The system of claim 16, wherein the threshold includes a baseline value of nominal surface charge for a plurality of contact regions of the screen.

18. The system of claim 9, wherein the instructions further comprise to: receive an indication of a manual actuation from a switch coupled to the display; and in response thereto, control the actuation.

19. The system of claim 9, wherein the at least one predetermined criteria includes failing to receive an input to abort the actuating (c) in response to a notification of an intent to perform the actuating (c) sent upon determining that the state of the transmission is in PARK.

* * * * *